United States Patent
Stahl et al.

(10) Patent No.: US 10,588,965 B2
(45) Date of Patent: Mar. 17, 2020

(54) FUCOSYLLACTOSE AS BREAST MILK IDENTICAL NON-DIGESTIBLE OLIGOSACCHARIDE WITH NEW FUNCTIONAL BENEFIT

(71) Applicant: N.V. Nutricia, Zoetermeer (NL)

(72) Inventors: Bernd Stahl, Utrecht (NL); Alma Jildou Nauta, Utrecht (NL); Johan Garssen, Utrecht (NL); Eric Samain, Gieres (FR); Sophie Drouillard, Claix (FR)

(73) Assignee: N.V. Nutricia, Zoetermeer (NL)

( * ) Notice: Subject to any disclaimer, the term of this patent is extended or adjusted under 35 U.S.C. 154(b) by 0 days.

(21) Appl. No.: 15/866,667

(22) Filed: Jan. 10, 2018

(65) Prior Publication Data

US 2018/0264104 A1 Sep. 20, 2018

Related U.S. Application Data

(63) Continuation of application No. 14/869,436, filed on Sep. 29, 2015, now abandoned, which is a continuation of application No. 13/383,822, filed as application No. PCT/NL2010/050447 on Jul. 12, 2010, now abandoned.

(60) Provisional application No. 61/256,453, filed on Oct. 30, 2009.

(30) Foreign Application Priority Data

Jul. 15, 2009 (EP) .................................... 09165485

(51) Int. Cl.
| | |
|---|---|
| A61K 39/39 | (2006.01) |
| A61K 31/702 | (2006.01) |
| A61P 37/04 | (2006.01) |
| A23L 29/30 | (2016.01) |
| A23L 33/00 | (2016.01) |
| A23L 33/10 | (2016.01) |
| A61P 31/12 | (2006.01) |
| A61K 31/7032 | (2006.01) |
| A23L 33/125 | (2016.01) |
| A23L 5/00 | (2016.01) |
| A61K 39/00 | (2006.01) |

(52) U.S. Cl.
CPC ............. *A61K 39/39* (2013.01); *A23L 29/30* (2016.08); *A23L 33/10* (2016.08); *A23L 33/40* (2016.08); *A61K 31/702* (2013.01); *A61K 31/7032* (2013.01); *A61P 31/12* (2018.01); *A61P 37/04* (2018.01); *A23L 5/00* (2016.08); *A23L 33/125* (2016.08); *A23V 2002/00* (2013.01); *A61K 2039/55* (2013.01); *A61K 2039/572* (2013.01)

(58) Field of Classification Search
None
See application file for complete search history.

(56) References Cited

U.S. PATENT DOCUMENTS

| | | | |
|---|---|---|---|
| 5,002,759 | A | 3/1991 | Gaffar et al. |
| 6,576,251 | B1 | 6/2003 | Stahl et al. |
| 8,591,919 | B2 | 11/2013 | Stahl et al. |
| 9,566,291 | B2 | 2/2017 | Boehm et al. |
| 2002/0019991 | A1 | 2/2002 | Prieto et al. |
| 2007/0274983 | A1 | 11/2007 | Kluijtmans et al. |
| 2007/0275881 | A1 | 11/2007 | Morrow et al. |
| 2008/0124323 | A1 | 5/2008 | Boehm et al. |
| 2008/0145838 | A1 | 6/2008 | Suda et al. |
| 2009/0221486 | A1* | 9/2009 | Schmitt ................ A23C 9/1234 514/6.9 |
| 2012/0178674 | A1 | 7/2012 | Stahl et al. |

FOREIGN PATENT DOCUMENTS

| | | |
|---|---|---|
| EP | 1 105 002 B2 | 6/2001 |
| EP | 1 597 978 A1 | 11/2005 |
| EP | 1 629 850 A1 | 3/2006 |
| EP | 2 072 052 A1 | 6/2009 |
| WO | WO 99/11773 A1 | 3/1999 |
| WO | WO 99/56754 A1 | 11/1999 |
| WO | WO-00/08948 A2 | 2/2000 |
| WO | WO 01/64225 A1 | 9/2001 |
| WO | WO-2005/039319 A2 | 5/2005 |
| WO | WO 2005/039597 A2 | 5/2005 |
| WO | WO 2005/055944 A2 | 6/2005 |
| WO | WO 2007/010084 A2 | 1/2007 |
| WO | WO 2007/067053 A1 | 6/2007 |
| WO | WO 2007/105945 A2 | 9/2007 |
| WO | WO-2007/114683 A1 | 10/2007 |
| WO | WO-2009/065905 A2 | 5/2009 |
| WO | WO-2009/077352 A1 | 6/2009 |
| WO | WO 2011/008086 A1 | 1/2011 |

OTHER PUBLICATIONS

Haug et al., "Bovine milk in human nutrition—a review" Lipids in Health and Disease vol. 6 No. 25 pp. 1-16 (Year: 2007).*
Vandenplas, "Oligosaccharides in Infant Formula," British Journal of Nutrition (2002) vol. 87, Suppl. 2, pp. S293-S296.
Kohlhuber, et al. "Breastfeeding rates and duration in Germany: a Bavarian cohort study", British Journal of Nutrition (May 2008), vol. 99, No. 5, pp. 1127-1132 [Epub Feb. 25, 2008].
Hesseling, et al. "Consensus statement on the revised World Health Organization recommendations for BCG vaccination in HIV-infected infants", Int J Tuberc Lung Disc (2008), vol. 12, No. 12, pp. 1376-1379.
Charlwood, et al. "A detailed analysis of Neutral and Acidic Carbohydrates in Human Milk", Analytical Biochemistry, 1999, vol. 273, pp. 261-277.

(Continued)

*Primary Examiner* — Eric Olson
(74) *Attorney, Agent, or Firm* — Gilberto M. Villacorta; Sunit Talaparta; Foley & Lardner LLP

(57) ABSTRACT

The invention concerns nutritional compositions with fucosyllactose for use in stimulation of NK cells. The composition is suitable for infants.

9 Claims, No Drawings

(56) References Cited

OTHER PUBLICATIONS

Fanaro, et al. "Galacto-oligosaccharides and long-chain fructo-oligosacchardies as prebiotics in infant formulas: A review", Acta Pediatrica, 2005, vol. 94, Suppl 449, pp. 22-26.
Mitoulas, et al. "Variation in fat, lactose and protein in human milk over 24 h and througout the first year of lactation", British Journal of Nutrition, 2002, vol. 88, pp. 29-37.
Urashima T. et al., "Oligosaccharides of milk and colostrum in non-human mammals", Glycoconjugate Journal, 2001, vol. 18, pp. 357-371.
Oftedal, O. T. "Lactation in the Dog: Milk Composition and Intake by Puppies", The Journal of Nutrition, vol. 114, 803-812, 1984.
Grollman, et al. "Biosynthesis of Fueosyllactose and Other Oligosaccharides Found in Milk", The Journal of Biological Chemistry, vol. 240, No. 3, Mar. 1965.
Carver J D. "Advances in nutritional modifications of infant formulas", Am J Clin Nutr, 2003, vol. 77(suppl) 1550S-1554S.
Ruiz-Palacios,et al. "Campylobacter jejuni Binds Intestinal H(O) Antigen (Fucα1, 2GalB1,4GlcNAc), and Fucosyloligosaccharides of Human Milk Inhibit Its Binding and Infection", The Journal of Biological Chemistry, Issue of Apr. 18, 2003, vol. 278, No. 16, pp. 14112-14120.
Childhood Vaccine Schedule (internet download, published in spring 2008), NIH Medline Plus, online date Apr. 10, 2013, 2 pgs.
Dog Vaccination Schedule (Internet download, publication date Nov. 29, 2008).
Zoppi G et al., Diet and antibody response to vaccinations in healthy infants. Lancet. Jul. 2, 1983;2(8340); 11-4.
Sumiyoshi W et al., Determination of each neutral oligosaccharide in the milk of Japanese women during the course of lactation. Br J Nutr. Jan. 2003; 89(1); 61-9.
Milk Facts—Nutritional Components in Milk. [online]Retrieved Oct. 23, 2012 from the internet http://www.milkfacts.info/Nutrition%20Facts/Nutritional%20Components.htm.
Sotgiu et al., "Immunomodulation of fucosyl-lactose and lacto-N-fucopentaose on mononuclear cells from multiple sclerosis and healthy subjects", International Journal of Biomedical Science, 2006, vol. 2, No. 2, pp. 114-120.
Search Report in International Application No. PCT/NL2010/050447 dated Oct. 19, 2010.
Benyacoub et al., "Feeding a diet containing a fructooligosaccharide mix can enhance *salmonella* vaccine efficacy in mice", Journal of Immunology, 2008, pp. 123-129.
Claud et al., "Hypothesis: inappropriate colonization of the premature intestine can cause neonatal necrotizing enterocolitis", The FASEB Journal, Aug. 2017, vol. 15, No. 8, pp. 1398-1403.
Faldella et al., "The preterm infant's antibody response to a combined diphtheria, tetanus, acellular pertussis and hepatitis B vaccine", Vaccine, 1998, vol. 16, No. 17, pp. 1646-1649.
Minna-Maija et al., "Fecal microflora in healthy infants born by different methods of delivery: Permanent changes in intestinal flora after Cesarean delivery", Journal of Pediatric Gastroenterology & Nutrition, Jan. 1999, vol. 28, No. 1, pp. 19-25.
"Bioprocesses and Biotechnology for Functional Foods and Nutraceuticals", Ed. Neeser & German, 2005, pp. 104-105.
"Prebiotics in infant nutrition" S. Donovan, G. Gibson, D. Newburg,—Mead Johnson Nutr. 2008, pp. 1-37.
Annex E filed with letter of patentee on Dec. 3, 2008 in appeal proceedings relating to the opposition of the grant of EP1105002 (E17b).
Boards of Appeal of the European Patent Office Communication T0918/05 issued in European Application No. 99941588.8 dated Mar. 3, 2009.
Bode, "Recent advances on structure, metabolism, and function of human mil k oligosaccharides", The journal of nutrition recent advances in nutritional Sciences, 2006, vol. 136, pp. 2127-2130.
Crittenden et al., "Production, properties and applications of food-grade oligosaccharides", Trends in Food Science& Technology, 1996, vol. 71, pp. 353-361.
Environ "GRAS Exemption claim for galacto-oligosaccharides (GOS)"application Vivinal (R), 2007, pp. 1-4.
Environ, "Generally Recognized as Safe (GRAS) Determination for the Use of Galacto-Oligosaccharides (GOS) in Foods and Term Infant Formulas", Vivinal (R), pp. 1-4, Sep. 6, 2007.
Hawley, The Condensed Chemical Dictionary, 10th ed. 1981.
Interlocutory decision in oppositions proceedings (Art. 101(3)(a) and 106(2) EPC) issued in European Application No. 04 077 394.7 dated Jul. 20, 2012.
Kidd, "Th1/Th2 Balance: The Hypothesis, its limitations, and implications for health and diseas", Alt Med Review, 2003, vol. 8, No. 3, pp. 223-246.
Kovarik et al., "Optimization of vaccine responses in early life: The role of delivery systems and immunomodulators", Immunol Cell Biol, 1998, vol. 76, pp. 222-236.
Letter patentee dated Sep. 10, 2012, in reply to communication under Rule 161(1) EPC in European Application No. 10734842.7.
Morrow et al., "Human-milk glycans that inhibit pathogen binding protect breast-feeding infants against infectious diarrhea", The Journal of Nutrition, 2005, vol. 135, No. 5, pp. 1304-1307.
Nakamura et al, "The milk oligosaccharides of domestic farm animals", Trends in glycoscience and glycotechnology, 2004, vol. 16, No. 88, pp. 135-142.
Newburg et al., "Innate protection conferred by fucosylated oligosaccharides of human milk against diarrhea in breastfed infants", Glycobiol, 2004, vol. 14, No, 3, pp. 25-263.
Newburg et al., "Neonatal protection by an innate immune systems of human milk consisting of oligosaccharides and glycans", J Anim Sci, 2009, vol. 87, pp. 26-34.
Ninonuevo et al., "Infant formula oligosaccharides opening the gates (for speculation)", Pediatric research, 2008, vol. 64, No. 1, pp. 8-10.
Nittynen et al., "Galacto-oligosaccharides and bowel function", Scan. J. Food Nutr., 2007, vol. 51, No. 2, pp. 62-66.
Torres et al., "Galacto-oligosaccharides: production, properties, applications, and significance as prebiotics", Comprehensive Reviews in Food Science and Food Safety, 2010, vol. 9, pp. 438-454.
Vos et al., "A specific prebiotic oligosaccharide mixture stimulates delayed-type hypersensitivity in a murine influenza vaccination model", Int. Immunopharmacol., 2006, vol. 6, pp. 1277-1286.
Vos et al., "Dietary supplementation of neutral and acidic oligosaccharides enhances Th1-dependent vaccination responses in mice", Pediatr. Allergy Immunol., 2007, vol. 18, pp. 304-312.

* cited by examiner

FUCOSYLLACTOSE AS BREAST MILK IDENTICAL NON-DIGESTIBLE OLIGOSACCHARIDE WITH NEW FUNCTIONAL BENEFIT

CROSS-REFERENCE TO RELATED APPLICATIONS

This application is a Continuation of U.S. patent application Ser. No. 14/869,436, filed Sep. 29, 2015, which is a Continuation of U.S. patent application Ser. No. 13/383,822, filed Mar. 28, 2012, which is the U.S. National Stage Application of PCT/NL2010/050447, filed Jul. 12, 2010, which claims the benefit of U.S. Provisional Patent Application No. 61/256,453, filed Oct. 30, 2009, and European Patent Application No. 09165485.5, filed Jul. 15, 2009, all of which are incorporated by reference in their entirety.

FIELD OF THE INVENTION

The present invention relates to infant nutrition with non-digestible oligosaccharides, in particular to the use thereof for stimulating the immune system.

BACKGROUND OF THE INVENTION

Human milk fed infants have a lower incidence of infections, including viral infections, than formula fed infants. Many components in human milk, including immunoglobulins (such as IgA), interleukin (IL)-1, IL-6, IL-8, IL-10, interferon-γ (IFN-γ), immunocompetent cells, transforming growth factor-β (TGF-β), lactoferrin, nucleotides, and non-digestible oligosaccharides (NDO) are thought to be involved in protection against infection with enteric or respiratory pathogens. TGF-β and dietary nucleotides were found to be components which may be responsible for increase in natural killer cell activity.

NDO are a major constituent of human milk and are a major element of the innate immune system of human milk. Human NDO promote the growth of a beneficial microbiota dominated by bifidobacteria and lactobacilli. Some human NDO are also known to be able to prevent directly the adhesion of pathogens and toxins.

Human milk is the preferred food for infants. However, it is not always possible or desirable to breast feed an infant. In such cases infant formulae or follow on formulae are a good alternative.

These formulae should have an optimal composition in order to mimic the beneficial effects of breast milk as close as possible.

WO 2007/067053 discloses infant formula comprising the plant-derived prebiotics inulin and galacturonic acid oligosaccharide and the from lactose synthesized prebiotic transgalacto-oligosaccharide to reduce infections.

WO 2007/010084 discloses mannan-poly- and oligosaccharides for immune stimulation.

U.S. Pat. No. 6,576,251 discloses a carbohydrate mixture for dietetic foods administered by the enteral or parenteral route consisting of (a) monosaccharide(s), (b) oligosaccharide(s) (at most hexasaccharides) and (c) polysaccharide(s) (at least heptasaccharides), where the mixing ratio a, b, c, in respect of weight, is: alpha=1, b=40 to 1000, and c=1 to 50, and containing at least 1 weight percent of fucose occurring either freely and/or bound to an oligosaccharide and/or a polysaccharide. The carbohydrate mixture is said to have both a nutritional and a biological effect which is considerably greater than the corresponding action of the individual constituents.

EP 1 629 850 provides a method and composition for the treatment and/or prevention of respiratory tract infection and/or respiratory tract infection disease, said method comprising orally administering a composition to a mammal, said composition comprising a galactose containing indigestible oligosaccharide and at least 5 wt. % digestible galactose saccharide.

EP 2 072 052 relates to a composition suitable for use in the prevention of opportunistic infections in immune-compromised individuals comprising a probiotic and a fucosylated oligosaccharide selected from the group comprising 2'-fucosyllactose, 3'fucosyllactose, difucosyllactose, lacto-N-fucopentaose, lacto-N-fucohexaose, fucosyllacto-N-hexaose and fucosyllacto-N-neohexaose. The document further discloses the use of such a composition in the prevention of opportunistic infections in immune-compromised individuals.

SUMMARY OF THE INVENTION

Human milk differs from milk from domestic animals in that it comprises more NDO and in that the NDO are structurally different. The group of human NDO is very complex, since it represents a heterogenic group of more than 130 different compounds with diverse sugar composition. Because of their complex and polymorphic structure, large-scale synthesis is complicated. It is therefore not yet technically and economically feasible to prepare infant nutrition with an NDO composition identical to human milk.

Recently, new techniques have become available to chemically synthesise specific types of NDO identical to specific human NDO, thereby offering the opportunity to test the immunomodulatory capacity of specific human NDO in in vitro and in vivo assays.

The inventors unexpectedly have found that fucosyllactose (FL), an oligosaccharide abundantly present in human breast milk and with a relatively simple structure, specifically increases the number and thereby the activity of Natural Killer (NK) cells. NK cells play an important role in the natural defence against viral infections and tumour cells. The finding which specific oligosaccharide is responsible for increasing NK cell activity now enables the design of nutritional compositions comprising FL, more particularly 2'-FL, for the use of increasing NK cells and/or NK cell activity.

DETAILED DESCRIPTION

The present invention thus concerns a method for stimulating NK cell activity and/or NK cell proliferation in a subject, said method comprising administering a composition comprising fucosyllactose to said subject, said composition not being human milk. In one embodiment the present method is a non-medical method for stimulating NK cell activity and/or NK cell proliferation in a subject. In one embodiment the present method is for treating and/or preventing viral infections in a subject.

The present invention also concerns a method for treating and/or preventing viral infections in a subject, said method comprising administering a composition comprising fucosyllactose to said subject, said composition not being human milk.

The invention can also be worded as the use of fucosyllactose in the manufacture of a composition for stimulating NK cell activity and/or NK cell proliferation, said composition not being human milk. In one embodiment the composition is for treating and/or preventing viral infections.

The invention can also be worded as the use of fucosyllactose in the manufacture of a composition for treating and/or preventing viral infections, said composition not being human milk.

The invention can also be worded as a composition comprising fucosyllactose for stimulating, in particular for use in stimulating, NK cell activity and/or NK cell proliferation, said composition not being human milk. In one embodiment the composition is for use in treating and/or preventing, viral infections.

The invention can also be worded as a composition comprising fucosyllactose for treating and/or preventing, in particular for use in treating and/or preventing, viral infections, said composition not being human milk.

The invention also concerns a method for treating and/or preventing infections, by stimulating natural killer (NK) cell activity and/or NK cell proliferation, said method comprising administering a composition comprising fucosyllactose to said subject, said composition not being human milk.

The invention can also be worded as the use of fucosyllactose in the manufacture of an enteral composition for treating and/or preventing infections, by stimulating natural killer (NK) cell activity and/or NK cell proliferation, said composition not being human milk.

The invention can also be worded as a composition comprising fucosyllactose for treating and/or preventing infections, in particular for use in and/or preventing infections, by stimulating natural killer (NK) cell activity and/or NK cell proliferation, said composition not being human milk.

The invention also concerns a method for enhancing vaccination response, said method comprising administering a composition comprising fucosyllactose to said subject, said composition not being human milk. In one embodiment the method is for enhancing vaccination response to vaccination with viral antigens.

The invention can also be worded as the use of fucosyllactose in the manufacture of an enteral composition for enhancing vaccination response. In one embodiment the composition is for enhancing vaccination response to vaccination with viral antigens.

The invention can also be worded as a composition comprising fucosyllactose for enhancing, in particular for use in enhancing, vaccination response. In one embodiment the composition is for enhancing vaccination response to vaccination with viral antigens.

The composition that is administered according to the present method, or that is used according to the present invention, is preferably enterally administered, more preferably orally. Or in other words the composition is preferably for enteral, preferably oral administration or in other words the composition is an enteral, preferably oral, composition.

Fucosyllactose

The present composition comprises fucosyllactose. Fucosyllactose (FL) is a non-digestible oligosaccharide present in human milk. It is not present in bovine milk. It consists of three monose units, fucose, galactose and glucose linked together. Galactose linked to glucose via a beta 1→4 linkage is called lactose. A fucose unit is linked to a galactose unit of a lactose via an alpha 1,2 linkage (2'-fucosyllactose, 2'-FL) or to the glucose unit of lactose via an alpha 1,3 linkage (3-fucosyllactose, 3-FL). The present composition preferably comprises 2'-FL.

2'-FL, preferably α-L-Fuc-(1→2)-β-D-Gal-(1→4)-D-Glc, and 3-FL, preferably α-L-Fuc-(1→3)-[β-D-Gal-(1→4)]-D-Glc), are commercially available for instance from Sigma-Aldrich. Alternatively, they can be isolated from human milk, for example as described in Andersson & Donald, 1981, J Chromatogr. 211:170-1744, or produced by genetically modified micro-organisms, for example as described in Albermann et al, 2001, Carbohydrate Res. 334:97-103.

Preferably, the composition comprises 1 mg to 3 g fucosyllactose per 100 ml, more preferably 10 mg to 2 g, even more preferably 20 mg to 100 mg FL per 100 ml. Based on dry weight, the composition preferably comprises 0.007 wt % to 20 wt % fucosyllactose, more preferably 0.07 wt % to 10 wt %, even more preferably 0.15 wt % to 1 wt %. A lower amount of fucosyllactose will be less effective in increasing NK cells and/or increasing NK cell activity, whereas a too high amount will result in unnecessary high costs of the product.

Non-Digestible Oligosaccharides Other than FL

The present composition preferably comprises non-digestible oligosaccharides (NDO) other than FL. Preferably the NDO other than FL stimulate the growth of bifidobacteria and/or lactobacilli, more preferably bifidobacteria. An increased content of bifidobacteria and/or lactobacilli stimulate the formation of a healthy intestinal microbiota. The NDO are preferably not or only partially digested in the intestine by the action of acids or digestive enzymes present in the human upper digestive tract, in particular in the small intestine and stomach, and are fermented by the human intestinal microbiota. For example, sucrose, lactose, maltose and the common maltodextrins are considered digestible.

Preferably the present composition comprises non-digestible oligosaccharides with a DP in the range of 2 to 250, more preferably 2 to 60. The non-digestible oligosaccharide is preferably at least one, more preferably at least two, preferably at least three selected from the group consisting of fructo-oligosaccharides, galacto-oligosaccharides, xylo-oligosaccharides, arabino-oligosaccharides, arabinogalacto-oligosaccharides, gluco-oligosaccharides, chito-oligosaccharides, glucomanno-oligosaccharides, galactomanno-oligosaccharides, mannan-oligosaccharides, sialic acid comprising oligosaccharides, and uronic acid oligosaccharides. The group of fructo-oligosaccharides includes inulins, the group of galacto-oligosaccharides includes transgalacto-oligosaccharides or beta-galacto-oligosaccharides, the group of gluco-oligosaccharides includes cyclodextrins, gentio- and nigero-oligosaccharides and non-digestible polydextrose, the group of galactomanno-oligosaccharides includes partially hydrolyzed guar gum, and the group of uronic acid oligosaccharides includes galacturonic acid oligosaccharides and pectin degradation products.

More preferably the present composition comprises at least one, more preferably at least two, most preferably three selected from the group consisting of fructo-oligosaccharides, beta-galacto-oligosaccharides and uronic acid oligosaccharides. More preferably the composition comprises beta-galacto-oligosaccharides.

In a preferred embodiment the composition comprises a mixture of inulin and short chain fructo-oligosaccharides. In a preferred embodiment the composition comprises a mixture of galacto-oligosaccharides and fructo-oligosaccharides selected from the group consisting of short chain fructo-oligosaccharides and inulin, more preferably inulin. A mixture of at least two different non-digestible oligosaccharides advantageously stimulates the beneficial bacteria of the intestinal microbiota to a greater extent. Preferably the weight ratio in a mixture of the two different non-digestible oligosaccharides, preferably galacto-oligosaccharides and fructo-oligosaccharide, is between 25 and 0.05, more preferably between 20 and 1. Galacto-oligosaccharides, preferably beta-galacto-oligosaccharides, are more capable of stimulating bifidobacteria. Preferably the present composition comprises galacto-oligosaccharides, preferably beta-galacto-oligosaccharides, with a degree of polymerization (DP) of 2 to 10 and/or fructo-oligosaccharides with a DP of 2 to 60.

The galacto-oligosaccharides preferably are beta-galacto-oligosaccharides. In a particularly preferred embodiment the present composition comprises beta-galacto-oligosaccharides ([galactose]n-glucose; wherein n is an integer ranging from 2 to 60, i.e. 2, 3, 4, 5, 6, . . . , 59, 60; preferably n is selected from 2, 3, 4, 5, 6, 7, 8, 9, and 10), wherein the galactose units are in majority linked together via a beta linkage. Beta-galacto-oligosaccharides are also referred to as trans-galacto-oligosaccharides (TOS). Beta-galacto-oligosaccharides are for example sold under the trademark Vivinal™ (Borculo Domo Ingredients, Netherlands). Another suitable source is Bi2Munno (Classado). Preferably the TOS comprises at least 80% beta-1,4 and beta-1,6 linkages based on total linkages, more preferably at least 90%.

Fructo-oligosaccharide is a NDO comprising a chain of beta-linked fructose units with a DP or average DP of 2 to 250, more preferably 2 to 100, even more preferably 10 to 60. Fructo-oligosaccharide includes inulin, levan and/or a mixed type of polyfructan. An especially preferred fructo-oligosaccharide is inulin. Fructo-oligosaccharide suitable for use in the compositions is also commercially available, e.g. Raftiline®HP (Orafti). Preferably the fructo-oligosaccharide has an average DP above 20.

Uronic acid oligosaccharides are preferably obtained from pectin degradation products. Hence the present composition preferably comprises a pectin degradation product with a DP of 2 to 100. Preferably the pectin degradation product is prepared from apple pectin, beet pectin and/or citrus pectin. Preferably the uronic acid oligosaccharide is a galacturonic acid oligosaccharide. Preferably the composition comprises FL and one of the group selected from galacto-oligosaccharide and uronic acid oligosaccharide.

Besides FL, most preferably the composition comprises beta-galacto-oligosaccharide, fructo-oligosaccharide and a uronic acid oligosaccharide. It was found that such a combination acts synergistically with fucosyllactose, in particular 2'-fucosyllactose. The weight ratio beta-galacto-oligosaccharide:fructo-oligosaccharide:uronic acid oligosaccharide is preferably (20 to 2):1:(1 to 20), more preferably (20 to 2):1:(1 to 10), even more preferably (20 to 2):1:(1 to 3), even more preferably (12 to 7):1:(1 to 2). Most preferably the weight ratio is about 9:1:1.1.

Preferably the weight ratio FL to beta-galacto-oligosaccharide, preferably TOS, is from 5 to 0.05, more preferably 5 to 0.1, more preferably from 2 to 0.1. Preferably the weight ratio FL to fructo-oligosaccharide, preferably inulin, is from 10 to 0.05, more preferably 10 to 0.1, more preferably from 2 to 0.5. Preferably the weight ratio FL to uronic acid oligosaccharide, preferably derived from pectin, is from 10 to 0.05, more preferably 10 to 0.1 more preferably from 2 to 0.5.

Preferably, the composition comprises 80 mg to 4 g non-digestible oligosaccharides, including fucosyllactose, per 100 ml, more preferably 150 mg to 2 g, even more preferably 300 mg to 1 g non-digestible oligosaccharides per 100 ml. Based on dry weight, the composition preferably comprises 0.25 wt % to 25 wt % non-digestible oligosaccharides including fucosyllactose, more preferably 0.5 wt % to 10 wt %, even more preferably 1.5 wt % to 7.5 wt %. A lower amount of non-digestible oligosaccharides will be less effective in stimulating the beneficial bacteria in the microbiota, whereas a too high amount will result in side-effects of bloating and abdominal discomfort.

Nutritional Composition

Preferably the composition comprising fucosyllactose is a nutritional composition. The composition of the present invention is not human milk. The present composition is preferably enterally administered, more preferably orally.

The present composition is preferably a nutritional formula, preferably an infant formula. The present composition can be advantageously applied as a complete nutrition for infants. The present composition preferably comprises a lipid component, protein component and carbohydrate component and is preferably administered in liquid form. The present invention includes dry food, preferably a powder, which is accompanied with instructions as to admix said dry food mixture with a suitable liquid, preferably with water.

The present invention advantageously provides a composition wherein the lipid component provides 5 to 50% of the total calories, the protein component provides 5 to 50% of the total calories, and the digestible carbohydrate component provides 15 to 85% of the total calories. The present invention advantageously provides a composition wherein the lipid component provides 20 to 50% of the total calories, the protein component provides 5 to 30% of the total calories, and the digestible carbohydrate component provides 30 to 70% of the total calories. Preferably, in the present composition the lipid component provides 35 to 50% of the total calories, the protein component provides 7.5 to 12.5% of the total calories, and the digestible carbohydrate component provides 40 to 55% of the total calories. For calculation of the % of total calories for the protein component, the total of energy provided by the proteins, peptides and amino acids needs to be taken into account.

The present composition preferably comprises at least one lipid selected from the group consisting of animal lipid, excluding human lipids, and vegetable lipids. Preferably the present composition comprises a combination of vegetable lipids and at least one oil selected from the group consisting of fish oil, animal oil, algae oil, fungal oil, and bacterial oil. The present composition preferably comprises long chain poly-unsaturated fatty acids (LC-PUFA). LC-PUFA are fatty acids or fatty acyl chains with a length of 20 to 24 carbon atoms, preferably 20 or 22 carbon atoms comprising two or more unsaturated bonds. More preferably the present composition comprises eicosapentaenoic acid (EPA, n-3), docosahexaenoic acid (DHA, n-3) and/or arachidonic acid (ARA, n-6).

Preferably the present composition comprises at least 0.1 wt. %, preferably at least 0.25 wt. %, more preferably at least 0.6 wt. %, even more preferably at least 0.75 wt. % LC-PUFA with 20 and 22 carbon atoms based on total fat content.

The content of LC-PUFA, particularly the LC-PUFA with 20 and 22 carbon atoms, preferably does not exceed 6 wt %, more preferably does not exceed 3 wt. % of the total fat content as it is desirable to mimic human milk as closely as possible. The LC-PUFA may be provided as free fatty acids, in triglyceride form, in diglyceride form, in monoglyceride form, in phospholipid form, or as a mixture of one of more of the above. The present composition preferably comprises between 5 and 75 wt. % polyunsaturated fatty acids based on total fat, preferably between 10 and 50 wt. %.

The protein used in the nutritional composition is preferably selected from the group consisting of non-human animal proteins (preferably milk proteins), vegetable proteins (preferably soy protein and/or rice protein), hydrolysates thereof, free amino acids and mixtures thereof. The present composition preferably contains casein, whey, hydrolyzed casein and/or hydrolyzed whey protein. Preferably the protein comprises intact proteins, more preferably intact bovine whey proteins and/or intact bovine casein proteins.

The present composition preferably contains digestible carbohydrates selected from the group consisting of sucrose, lactose, glucose, fructose, corn syrup solids, starch and maltodextrins, more preferably lactose.

In view of the above, it is also important that the liquid food does not have an excessive caloric density, however still provides sufficient calories to feed the subject. Hence, the liquid food preferably has a caloric density between 0.1 and 2.5 kcal/ml, even more preferably a caloric density of between 0.5 and 1.5 kcal/ml, most preferably between 0.6 and 0.8 kcal/ml.

Preferably the present composition comprises nucleotides and/or nucleosides, more preferably nucleotides. Preferably, the composition comprises cytidine 5'-monophospate, uridine 5'-monophospate, adenosine 5'-monophospate, guanosine 5'-monophospate, and/or inosine 5'-monophospate, more preferably cytidine 5'-monophospate, uridine 5'-monophospate, adenosine 5'-monophospate, guanosine 5'-monophospate, and inosine 5'-monophospate. Preferably the composition comprises 5 to 100, more preferably 5 to 50 mg, most preferably 10 to 50 mg nucleotides and/or nucleosides per 100 gram dry weight of the composition. The presence of nucleotides and/or nucleotides advantageously stimulates NK cell activity. The nucleotides and/or nucleosides are deemed to act synergistically with the fucosyllactose of the present composition.

Application

In one embodiment the present composition is used for stimulating natural killer cell activity and/or natural killer cell proliferation. In one embodiment the present composition is used for treating and/or preventing viral infections. In one embodiment the composition for stimulating natural killer cell activity and/or natural killer cell proliferation, and/or for treating and/or preventing viral infections is for administering to HIV patients, elderly and/or oncology patients.

NK cells are a type of cytotoxic lymphocytes that constitute a major component of the innate immune system. NK cells play a major role in defense against intracellular infections. NK-cells are defined as large granular lymphocytes that do not express T-cell antigen receptors (TCR) or Pan T marker CD3 or surface immunoglobulins (Ig) B cell receptor but that usually express the surface markers CD16 (FcγRIII) and CD56 in humans. They were named "natural killers" because of the initial notion that they do not require activation in order to kill cells that are missing "self" markers of major histocompatibility complex (MHC) class I. NK cells have two major types of effector function; cell killing and the secretion of cytokines. Increasing NK cell activity (by increasing the number of NK cells and/or by increasing the specific activity of an NK cell), results in an increased resistance against viral infections. The use of a nutritional composition comprising fucosyllactose is therefore preferably for preventing and/or treating viral infections, more preferably viral infections caused by orthomyxoviridae, in particular the influenza virus, herpesviridae, rotavirus, cytomegalovirus, caliciviridae, respiratory syncytial virus, human imunodeficiency virus and/or rhinovirus. The use of a nutritional composition comprising fucosyllactose is therefore preferably for preventing and/or treating viral infections, more preferably the viral infections common cold, flu, measles, chicken pox, viral diarrhoea, viral gastro-enteritis, HIV infection and/or viral respiratory tract infections. In a preferred embodiment the present invention is used for HIV patients. In one embodiment, the present invention concerns providing nutrition to a HIV patient. The present composition is advantageous for HIV patients since HIV patients have a decreased natural killer cell activity.

The use of a nutritional composition comprising fucosyllactose is therefore especially beneficial for infant formula. In one embodiment, the present invention concerns providing nutrition to an infant. Formula fed infants have an underdeveloped immune system compared with adults and are more prone to viral infections than human milk fed infants. Preferably the infant is from 0 to 36 months of age, more preferably of 0 to 18 months, even more preferably of 0 to 12 months, most preferably of 0 to 6 months of age. The younger the infant is, the less developed the immune system.

The composition comprising fucosyllactose even more advantageously is used in preterm infants and/or very low or low birth weight infants, since these infants are even more vulnerable and/or prone to viral infections.

The composition comprising fucosyllactose even more advantageously is used in infants delivered via Caesarean section. Caesarean section born infants are born in a hospital in an environment having more pathogens against which the antibodies, conferred by the mother to the infant, are not effective against. Caesarean section born infants have a delayed and less optimal colonization of the large intestinal tract and therefore are also more prone to intestinal infections.

The composition comprising fucosyllactose is advantageously used for nutrition for elderly. In one embodiment, the present invention concerns providing nutrition to an elderly person. An elderly person is a person having an age of 55 years or more, in particular of the age of 65 or more. Elderly have a demonstrated lower activity of natural killer cell activity than healthy young adult individuals. Elderly are especially vulnerable to viral infection complications. In a preferred embodiment the present invention is used for treatment and/or prevention of immunosenescence in elderly. Elderly are more prone to the development of tumours. NK cell activity suppresses tumour cell proliferation. In a preferred embodiment the present invention is used for nutrition in cancer patients. Oncology patients have a lower natural killer cell activity than healthy young adult individuals.

EXAMPLES

Example 1

Materials and Methods 6-8 Weeks old female C57BL/6 mice (Charles River) received semi-purified AIN-93G-based diets (Research Diet Service, Wijk bij Duurstede, the Netherlands), comprising 1) 2 wt % beta-galacto-oligosaccharide (GOS; source Vivinal GOS, Borculo Domo), fructo-oligosaccharide (FOS; source RaftilineHP, Orafti) and galacturonic acid oligosaccharide (Source AOS) in a 9:1:1.1 ratio. AOS are produced from pectin (Südzucker AG, Mannheim, Germany), with a DP of 1-20. It consists of approximately 75% galacturonic acid oligomers, based on total weight;

2) 1 wt % lactoneotetraose (LNnT), 3) 1 wt % 3'-sialyl lactose (3'-SL), or 4) 1 wt % 2'-fucosyllactose (2'-FL).

All groups were compared to the unsupplemented control diet. Dietary supplementation started 14 days before the first vaccination and lasted until the end of the experiment, 31 days after the first vaccination.

Vaccination experiments were performed using Influvac (Solvay Pharmaceuticals, Weesp, the Netherlands) from season 2005/2006. The mice received a primary vaccination and a booster vaccination, consisting of a subcutaneous (sc) injection of a 1:1 mix of vaccine and adjuvant in a total volume of 100 μl. The booster vaccination was given at 21 days after the primary vaccination. The experiments ended 10 days after booster vaccination. Blood samples were taken at the end of the experiment. Negative control groups that were included received injections with a 1:1 mix of PBS and adjuvant in a total volume of 100 μl. To determine the percentage of NK cells, cells were labelled with FITC-labelled anti-mouse CD3 mAb in combination with PE-labelled anti-mouse NK1.1 mAb. NK cell cytotoxicity in spleen cell suspensions was assayed using standard $^{51}Cr$ release assays. Briefly, NK cell cytotoxicity was tested using YAC-1 target cells. The percentage of specific $^{51}Cr$ release was calculated as the percentage of specific lysis=(experimental release−spontaneous release)/(total detergent release−spontaneous release)×100. The spontaneous release values were always <15% of total lysis.

The percentage of regulatory T cells (Treg) was determined by flow cytometry (FACSCalibur) using allophycocyanin (APC-)labelled anti-mouse CD3 mAb, Pe-Cy5-labeled anti-mouse CD4 mAb and phycoerythrin (PE)-labelled anti-mouse CD25 mAb in combination with intracellular staining of fluorescein-isotiocyanate (FITC)-labelled Foxp3 mAb, according to the instructions offered by the manufactures (eBiosciences, San Diego, Calif.).

Statistical analysis was performed using GraphPadPrism software. Statistical differences between test and control groups were analysed by ANOVA and post hoc Dunnett's test if multiple groups were compared to a single (control) group. P-values <0.05 were considered significant in all experiments.

Results

The immunomodulatory effect of three chemically synthesised human oligosaccharides was compared with GOS/FOS/AOS. Supplementation with GOS/FOS/AOS, LNnT, 2'-FL or 3'-SL resulted in a significant increase of the DTH response, a TH1-dependent parameter, compared with control-fed animals.

Interestingly, the percentage of NK cells in the spleen was significantly increased in mice supplemented with human oligosaccharides compared to control and GOS/FOS/AOS-supplemented mice, see table 1. This effect was highest with 2'-FL. To examine whether the increase in the percentage of NK cells in human oligosaccharides-supplemented groups also correlated with functional activity, NK cell activity was measured in mouse splenocytes. A significant increased NK cell activity was detected in the splenocytes of mice that were supplemented with 2'-FL compared to controls, see Table 1.

TABLE 1

Effect of dietary NDO similar to human milk NDO on NK cells and NK cell activity.

| Dietary intervention | % NK 1.1 + cells (SE) | NK cell activity, % lysis At E:T ratio 1:50 |
|---|---|---|
| Sham control | 2.5 (0.2) | 1.57 |
| Control | 2.2 (0.1) | 1.13 |
| GOS/FOS/AOS | 2.5 (0.1) | 1.95 |
| LNnT | 2.8 (0.1)* | 2.14 |
| 3'-SL | 3.0 (0.2)* | 1.93 |
| 2'-FL | 3.7 (0.1)** | 2.48* |

*indicates $p < 0.05$ compared to control group
**indicates $p < 0.01$ compared to control group Finally, the amount of regulatory T cells (Treg) was decreased to the highest extent with the diet with FL as can be seen in Table 2.

TABLE 2

Effect of dietary NDO similar to human milk NDO on percentage of regulatory T cells Treg.

| Dietary intervention | Treg percentage (s.e.m.) |
|---|---|
| Sham control | 3.6 (0.4) |
| Control | 3.9 (0.2) |
| GOS/FOS/AOS | 4.1 (0.3) |
| LNnT | 3.2 (0.2) |
| 3'-SL | 2.8 (0.2)* |
| 2'-FL | 2.8 (0.2)* |

*indicates $p < 0.05$ compared to control group

The decrease in regulatory T cells is indicative for a decreased inhibition of immune response and hence enables an increased vaccination response to the viral antigens. A temporarily decrease of regulatory T cells can be especially beneficial when vaccination is to occur.

Overall, these results support that oral supplementation with 2'-FL stimulates growth and/or activity of NK cells. These results are indicative for an effect of dietary 2'-FL for enhancing vaccination response, in particular vaccination with viral antigens. These results are indicative for an effect of dietary 2'-FL for treating and/or preventing viral infections.

Example 2

Infant formula for stimulating NK cell activity comprising per 100 ml (13.9 dry weight):

1.4 g protein (whey and casein)

7.3 g digestible carbohydrates (including lactose)

3.6 g fat (vegetable fat, fish oil)

0.8 g non-digestible oligosaccharides of which 80 mg 2'-fucosyllactose and 640 mg beta-galacto-oligosaccharides, and 80 mg fructo-oligosaccharides Further are included: choline, myo-inositol, taurine, minerals, trace elements, and vitamins as known in the art.

Example 3

A preferred composition that can be used for the stimulation of natural killer cell activity in HIV patients may comprise per 100 g dry weight.

| | |
|---|---|
| Dietary fibre | 5-50 g |
| Fructo-oligosaccharide | 5% of total dietary fibre |
| Galacto-oligosaccharide | 40% of total dietary fibre |
| Pectin hydrolysate | 50% of total dietary fibre |
| 2'-FL | 5% of total dietary fibre |
| N-acetyl cysteine | 0.5-5 g |
| Carbohydrate (not dietary fibre) | 2-20 g |
| Fat | 4-20 g |

The invention claimed is:

1. A method of enhancing a vaccination response, comprising administering to a subject in need thereof a composition comprising fucosyllactose, wherein the composition is not human milk.

2. The method according to claim 1, wherein the subject is an infant, HIV patient, elderly and/or oncology patient.

3. The method according to claim 1, wherein the composition additionally comprises at least one of beta-galacto-oligosaccharides, fructo-oligosaccharides and uronic acid oligosaccharides.

4. The method according to claim 1, wherein the fucosyllactose is 2'-fucosyllactose.

5. The method according to claim 1, wherein the composition comprises 0.07 to 1 wt % fucosyllactose based on dry weight of the composition.

6. The method according to claim 1, wherein the composition comprises 5 to 50% protein, 15 to 85% digestible carbohydrates and 5 to 50% fat based on total energy.

7. The method according to claim 1, for enhancing vaccination with viral antigens.

8. The method according to claim 1, wherein the subject is subsequently administered a vaccine.

9. The method according to claim 1, wherein the composition is administered 14 days before the subject is subsequently administered a vaccine.

* * * * *